United States Patent
Bredesen et al.

(10) Patent No.: US 6,649,364 B1
(45) Date of Patent: Nov. 18, 2003

(54) ANTI-APOPTOTIC COMPOSITIONS AND METHODS USING SAME

(75) Inventors: Dale E. Bredesen, Rancho Santa Fe, CA (US); Celik Kayalar, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 08/485,395

(22) Filed: Jun. 7, 1995

(51) Int. Cl.[7] .......................... C12Q 1/37; C12Q 1/48; G01N 33/53
(52) U.S. Cl. ..................... 435/23; 435/15; 435/7.71; 435/7.72; 435/7.9; 435/7.91
(58) Field of Search .................. 435/23, 7.71, 7.72, 435/15, 7.9, 7.91

(56) References Cited

PUBLICATIONS

Black et al., "Activation of interleukin–1β by a co–induced protease" *FEBS Lett.* 247 (2):386–390 (1989).
Boudreau et al., "Suppression of ICE and Apoptosis in Mammary Epithelial Cells by Extracellular Matrix" *Science* 267:891–893 (1993).
Forloni et al., "Neurotoxicity of a prion protein fragment" *Nature* 362:543–546 (1993).
Gagliardini et al., "Prevention of Vertebrate Neuronal Death by the crmA Gene" *Science* 263:826–828 (1994).
Kabsch et al., "Atomic structure of the actin:DNase I complex" *Nature* 347:37–44 (1990).
Linnik et al., "Evidence Supporting a Role for Programmed Cell Death in Focal Cerebral Ischemia in Rats" *Stroke* 24(12):2002–2009 (1993).
Mannherz et al., "The Interaction of Bovine Pancreatic Deoxyribonuclease I and Skeletal Muscle Actin", *Eur. J. Biochem.* 104:367–379 (1980).
Mattson et al., "β–Amyloid Peptides Destabilize Calcium Homeostasis and Render Human Cortical Neurons Vulnerable to Excitotoxicity", *J. Neurosci.* 12(2):376–389 (1992).
Miura et al., "Induction of Apoptosis in Fibroblasts by IL–1β–Converting Enzyme, a Mammalian Homolog of the C. elegans Cell Death Gene ced–3" *Cell* 75:653–660 (1993).
Peitsch et al., "Characterization of the endogenous deoxyribonuclease involved in nuclear DNA degradation during apoptosis (programmed cell death)" *EMBO J.* 12(1):371–377 (1993).
Poe et al., "Human Cytotoxic Lymphocyte Granzyme B" *J. Biol. Chem.* 266(1):98–103 (1991).
Ray et al., "Virtual Inhibition of Inflammation: Cowpox Virus Encodes an Inhibitor of the Interleukin–1β Converting Enzyme" *Cell* 69:597–604 (1992).
Scher, "Therapeutic Approaches to Alzheimer's Desease" *Bio/Technol.* 12:140–144 (1994).

Schwyter et al., "Subtilisin–Cleaved Actin: Polymerization and Interaction with Myosin Subfragment 1" *Biochemistry* 28(14):5889–5895 (1989).
Suck et al., "Three–dimensional structure of the complex of skeletal muscle actin and bovine pancreatic DNase I at 6–Å resolution" *Proc. Natl. Acad. Sci. USA* 78(7):4319–4323 (1981).
Thornberry et al., "A novel heterodimeric cysteine protease is required for interleukin–1β processing in monocytes" *Nature* 356:768–774 (1992).
Wang et al., "Ich–1, an Ice/ced–3–Related Gene, Encodes Both Positive and Negative Regulators of Programmed Cell Death" *Cell* 78:739–750 (1994).
Yuan and Horvitz, "The *Caenorhabditis elegans* Genes ced–3 and ced–4 Act Cell Autonomously to Cause Programmed Cell Death" *Dev. Biol.* 138:33–41 (1990).
Zychlinsky et al., "*Shigella flexneri* induces apoptosis in infected macrophages" *Nature* 358:167–169 (1992).
Howard et al., "IL–1–Converting Enyzme Requires Aspartic Acid Residues for Processing of the IL–1β Precursor at Two Distinct Sites and Does Not Cleave 31–kDa IL–1α" *J. Immunol.* 147(9):2964–2969 (1991).
Kakunaga et al., "A mutation in actin associated with neoplastic transformation" *Federation Proc.* 43(8):2275–2279 (1984).
Kayalar et al., "Cleavage of actin by inteleukin 1β–converting enzyme to reverse DNase I inhibition" *Proc. Natl. Acad. Sci. USA* 93:2234–2238 (1996).
Leavitt et al., "Expression of Transfected Mutant β–Actin Genes: Transitions toward the Stable Tumorigenic State" *Mol. Cell. Biol.* 7(7):2467–2476 (1987).
Mashima et al., "Identification of Actin as a Substrate of ICE and an ICE–like Protease and Involvement of an ICE–like Protease but not ICE in VP–16–Induced U937 Apoptosis" *Biochem. Biophys. Res. Comm.* 217(3):1185–1192 (1995).
Olson et al., "Angiogenin antagonist prevent tumor growth in vivo" *Proc. Natl. Acad. Sci. USA* 92(2):442–446 (1995).
Solomon et al., "Studies on the Role of Actin's Aspartic Acid 3 and Aspartic Acid 11 Using Oligodeoxynucleotide–directed Site–specific Mutagenesis" *J. Biol. Chem.* 263(236):19662–19669 (1988).
Xia et al., "Probing Actin Incorporation Into Myofibrils Using Asp11 and His73 Actin Mutants" *Cell Motility and Cytoskeleton* 26(2):115–124 (1993).

*Primary Examiner*—Gabrielle Bugaisky
(74) *Attorney, Agent, or Firm*—Gray Cary Ware & Freidenrich LLP

(57) ABSTRACT

The present invention provides methods and compositions for modulating the apoptotic activity of interleukin-1β converting enzyme (ICE).

The present invention further provides methods and compositions for alleviating pathological conditions associated with apoptotic mechanisms.

4 Claims, 1 Drawing Sheet

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 5 amino acids
      (B) TYPE: amino acid
      (D) TOPOLOGY: linear (ii) MOLECULE TYPE: peptide (xi) SEQUENCE DESCRIPTION: SEQ ID NO:1:

Gln Ala Cys Arg Gly
1              5

(2) INFORMATION FOR SEQ ID NO:2:

```
        (i) SEQUENCE CHARACTERISTICS:
            (A) LENGTH: 4 amino acids
            (B) TYPE: amino acid
            (D) TOPOLOGY: linear (ii) MOLECULE TYPE: peptide (xi) SEQUENCE DESCRIPTION: SEQ ID NO:2:

Tyr Val Ala Asp
1

(2) INFORMATION FOR SEQ ID NO:3:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (xi) SEQUENCE DESCRIPTION: SEQ ID NO:3:

Asn Gly Ser Gly Leu Val
1               5

(2) INFORMATION FOR SEQ ID NO:4:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (xi) SEQUENCE DESCRIPTION: SEQ ID NO:4:

Gly Gln Val Ile Thr Ile
1               5

(2) INFORMATION FOR SEQ ID NO:5:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO:5:

Ala Pro Leu Asn Pro
1               5
```

ANTI-APOPTOTIC COMPOSITIONS AND METHODS USING SAME

This invention was made in part with Government support under Grant No. AG 12282 from the National Institutes of Health (National Institute of Aging). The Government may have certain rights in this invention.

BACKGROUND OF THE INVENTION

Programmed cell death is recognized as an integral part of the biological repertoire of multicellular organisms where an intrinsic suicide mechanism can be activated either as a response to an invading pathogen or to specific signals generated during the normal course of the development of the animal. Apoptosis, from the Greek word for the falling off of leaves, is a morphologically distinct form of this death process hallmarks of which include plasma membrane bleb formation, retraction of cellular processes (e.g., neurite retraction during neuronal apoptosis), decrease in cellular volume, cellular rounding, nuclear fragmentation, and cellular budding to produce apoptotic bodies (Kerr J. F. R. and Harmon, B. V., 1991; *Cold Spring Harbor Laboratory Press:* New York, p. 321). The body utilizes apoptosis in many ways, including, for example, tissue remodeling during growth and development, deletion of autoreactive lymphocytes from the immune system, and elimination of cells containing damaged DNA.

Apoptosis-inducing stimuli are diverse, and include normal physiological signals, such as hormones that trigger deletion of cells during differentiation or involution of tissues or organs, maturation of organ systems as, for example, in the immune system, and removal of cells that have sustained some form of damage. Alternatively, cells may be already primed to undergo apoptosis, with removal of either intracellular apoptosis-inhibitory factors or withdrawal of important extracellular components, such as growth factors, providing the signal. Other apoptosis signals are also important from the biomedical perspective. These include radiation, hyperthermia, calcium influx, glucocorticoids and cytotoxic agents.

In adult tissues, apoptosis is involved in tissue homeostasis, physiological responses to hormones, and pathological response to pharmacological and toxic substances. Apoptotic deletion of cells is observed in both rapidly and slowly dividing tissues, for example in the intestinal crypts and the liver. Hormonal regulation of "cell growth" is often mediated by blocking apoptosis. For example, physiological lowering of trophic hormone levels results in apoptosis in the premenstrual endometrium and in the breast epithelium at the end of the menstrual cycle. In the prostate, testosterone inhibits apoptosis; removal of androgen stimulation by castration in rats results in regression and atrophy of the prostate due to cell death. Apoptosis also plays a major role in immunological control. During maturation of thymocytes, cells recognizing self-antigens are clonally deleted by apoptosis to allow immunological tolerance. In the liver, numerous drugs, hormones, and environmental toxins induce liver enlargement and promote preferentially the growth of preneoplastic foci. Regression of these foci following removal of the stimuli is often accompanied by extensive apoptosis, suggesting that these agents affect growth by blocking apoptosis. Radiation, mild hyperthermia, cancer chemotherapeutic agents, and chemical carcinogens induce apoptosis in certain cells and tissues. Apoptosis is observed to occur spontaneously in a wide variety of neoplasms.

Many infectious agents that modulate the immune system for their survival may do so by affecting the normal apoptosis process. It has been demonstrated that many viruses express anti-apoptotic factors as part of their initial, productive infection of mammalian cells (White and Gooding, "Regulation of apoptosis by human adenoviruses" p. 111–142 in *APOPTOSIS II: THE MOLECULAR BASIS OF APOPTOSIS IN DISEASE*, Tomei and Cope (Eds). Cold Spring Harbor Laboratory Press, New York (1994)). Infectious agents other than viruses also have been demonstrated to modulate apoptosis in vivo. (Zychlinski et al., *Nature* 358:167–169 (1992)).

Evidence for apoptosis in neurodegenerative disease has been obtained in chronic cases, such as Alzheimer's disease, multiple sclerosis, ataxia telangiectasia, and prion-induced neuronal cell death and also, in acute diseases such as stroke (Linnick et al., *Stroke* 24:2002–2009 (1993); Mattson et al., *J. Neurosci.* 12:376–389 (1992); Scher, R. S., *Bio/Technol.* 12:140–144 (1994); Olson, L., *Exp. Neur.* 124:5–15 (1993); Forloni et al., *Nature* 362:543–546 (1993)).

Other disease processes where disregulated apoptosis has been implicated include, for example, various malignant and pre-malignant conditions such as B cell lymphoma and chronic lymphocytic leukemia, heart disease such as ischemic cardiac damage and chemotherapy-induced myocardial suppression, immune system disorders such as AIDS and type I diabetes, intestinal disorders such as inflammatory bowel disease and radiation- and HIV-induced diarrhea, and kidney disease such as polycystic kidney disease and anemia/erythropoiesis.

Accordingly, disregulation of programmed cell death is variously implicated in human disease. Thus, there is a great clinical need to elucidate the underlying molecular basis of the apoptosis mechanism and its role in disease which, in turn, will enable the development of compositions and methods for modulating the proteolytic, endonucleolytic, and morphogenetic aspects of apoptosis. The present invention satisfies this need and provides related advantages as well.

SUMMARY OF THE INVENTION

The present invention provides methods and compositions for modulating the apoptotic activity of interleukin-1β converting enzyme (ICE).

The present invention further provides methods and compositions for alleviating pathological conditions associated with apoptotic mechanisms.

DETAILED DESCRIPTION OF THE INVENTION

Figure 1:
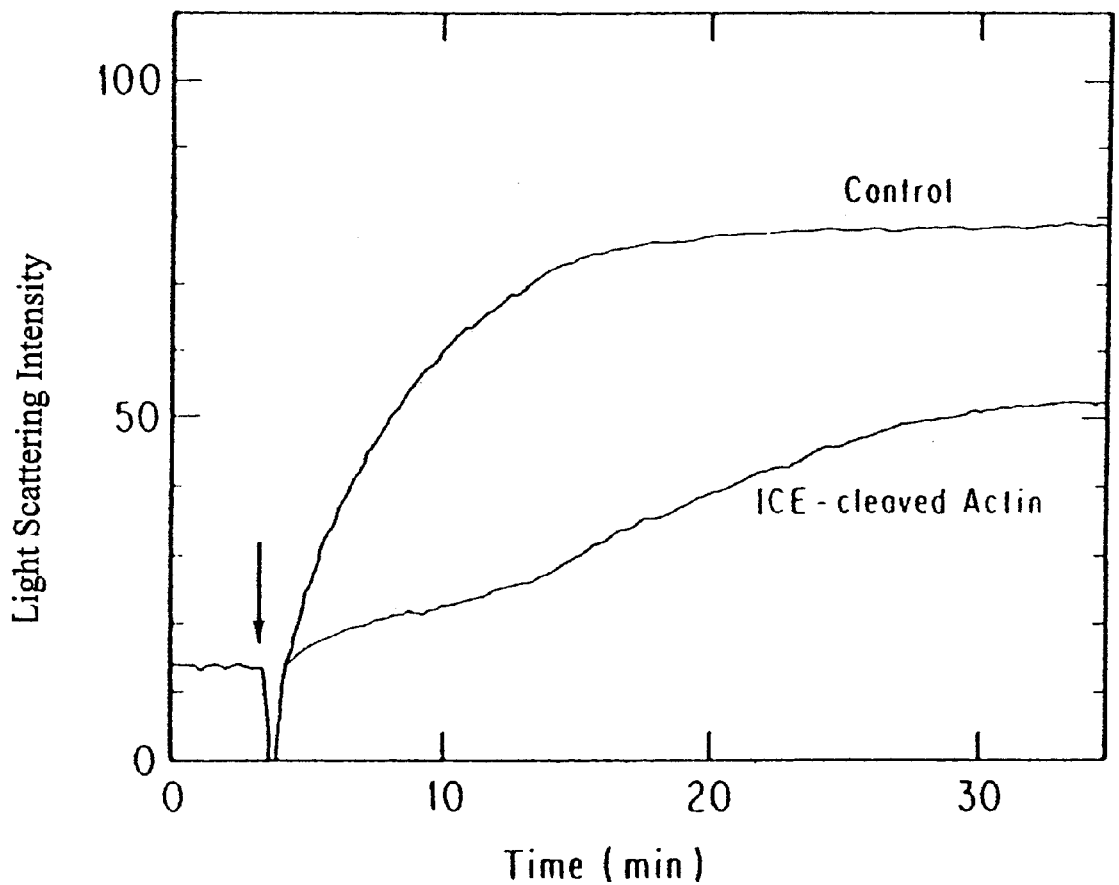
FIG. 1 shows the effect of ICE cleavage on the ability of actin to polymerize.

The cytokine interleukin-1 (IL-1) has been implicated in inflammation, septic shock, and other physiological situations, including wound healing and the growth of certain leukemias. There are two distinctly related forms of IL-1, α and β. Monocytes and macrophages synthesize IL-1β as an inactive 31 kd precursor (pro-IL-1β) that is proteolytically cleaved into the biologically active 17.5 kd form of the cytokine.

The cytoplasmic protease responsible for such cleavage has been identified as IL-1β converting enzyme (ICE). ICE cleaves pro-IL-1β at two sites releasing the 153 carboxy-terminal amino acids that constitute the mature hormone. Each cleavage sites contains an aspartyl residue at the P1 position (i.e., Asp$^{116}$-Ala$^{117}$ and Asp$^{244}$-Gly$^{245}$) (17, 18). Interestingly, the 45 kd ICE proenzyme similarly undergoes self-cleavage at aspartyl residues (i.e., 103, 119, 297 and 316) to generate the active enzyme. Active ICE is a heterodimer consisting of two subunits, P20 (20 kd) and Plo (10 kd), both of which are required for the enzyme activity of the mature protein.

Although many proteins have accessible aspartyl residues on their surfaces, the only natural protein substrate for ICE discovered to date, other than pro-IL-1β, has been the precursor form of ICE itself (14, 15). These findings suggest that ICE is a member of a new, structurally distinct class of cysteine proteases. The unusually high substrate specificity for a subset of Asp-X bonds within the pro-IL-1β molecule and the absence of homology to all known cysteine proteases places ICE in a new subclass of thiol proteases.

Other members of the large family of cysteine proteases have been identified. For example, programmed cell death in the nematode *C. elegans* requires the expression of the ced-3 and ced-4 genes (Yuan, J. and Horvitz, H. R., 1990; *Dev. Biol.* 138:33–41). The ced-3 gene product is similar (28% amino acid identity) to the mammalian ICE protease. The murine Nedd2 gene encodes a protein similar to ced-3 and mammalian ICE, and induces apoptosis when overexpressed in cultured fibroblast and neuroblastoma cells. The CPP32 gene has also been identified as a mammalian cysteine protease (19-21).

A critical function of the ICE protease is indicated by the finding that Crm A, a cowpox virus cytokine response modifier specifically inhibits the proteolytic activity of ICE in vitro (Ray, et al., 1992; *Cell* 69:597–604) also inhibits apoptosis when expressed in primary neuronal cultures (Gagliardini, et al., 1994; *Science* 263:826–828), Rat-1 fibroblast (Wang, et al., 1994; *Cell* 78:739–750) and mammary epithelial cells (Boudreau, et al., 1995; 267:891–893). Furthermore, overexpression of ICE has been shown to induce apoptosis in Rat-1 fibroblasts (Miura, et al., 1993; *Cell* 75:653–660) and HeLa cells (Wang, et al., 1994; *Cell* 78:739–750). These and similar recent reports with other members of the ICE/ced-3 family indicate that the proteolytic activity of ICE or an ICE-like protease is required for apoptosis.

In many tissues and cell-types that can undergo apoptosis but do not express IL-1β,ICE has been shown to be constitutively expressed, often simultaneously with other members of the ICE/ced-3 family. Therefore, the expression data alone do not allow a definite conclusion as to which family member(s) may actually be involved in apoptosis. At this stage, it is also conceivable that more than one family member may jointly contribute to the death process and that the extent and nature of a possible cooperation among the family members may be dependent on the cell-type and/or the apoptotic pathway activated upstream from the ICE/ced-3 family. Consistent with this possibility, recent reports demonstrate that thymocytes from mice deficient in ICE are sensitive to apoptosis induced by dexamethasone or ionizing radiation but are resistant to apoptosis induced by Fas antibodies.

The present invention demonstrates that actin is a substrate for the pro-apoptotic cysteine protease, ICE. Actin is cleaved by ICE mainly at two sites, Asp$^{11}$-Asn$^{12}$ and Asp$^{244}$-Gly$^{245}$. Time course studies demonstrate that Asp$^{11}$-Asn$^{12}$ is the initial site of proteolysis, followed by release of the cleaved actin, and then a subsequent cleavage at Asp$^{244}$-Gly$^{245}$. A minor cleavage site at Glu$^{107}$-Ala$^{108}$ is also identified. Accordingly, the findings reported herein provide a simple yet general model as to how the ICE protease, as well as other related proteases, function in apoptosis.

The internucleosomal fragmentation of DNA that occurs as part of apoptosis in most cells has been shown to be due to deoxyribonuclease I (DNase I). Full-length actin binds to and inhibits DNase I with an association constant of $10^9$ M$^{-1}$ (Mannherz, et al., 1980; *Eur. J. Biochem.* 104:367–379), and actin-DNase I complexes have been observed in vivo.

The significance of the cleavage of actin by ICE in the structural and biochemical changes associated with apoptosis is strongly supported by the following observations. First, alterations in actin occur early in apoptosis, and have been implicated in the formation of plasma membrane blebs, which appear early in most apoptosis paradigms (37–40). Second, prevention of actin polymerization may lead to process retraction; moreover, the addition of DNase I to F-actin induces rapid depolymerization (Suck, et al., 1981; *Proc. Natl. Acad. Sci. USA* 78:4319–4323). Thus, ICE cleavage of G-actin could conceivably lead to F-actin depolymerization both by destroying the ability of G-actin to polymerize and by increasing the local concentration of free DNase I, which could in turn depolymerize F-actin. Third, apoptosis has been shown to be induced by microfilament disruption by cytochalasin B (42) and by actin depolymerization with bis(tri-n-butyltin)oxide (39). Finally, DNase I has been implicated as the major endonuclease associated with the internucleosomal fragmentation of DNA that is characteristic of apoptosis in most paradigms. For example, antibodies specific for DNase I immunoprecipitate the nucleolytic activity; apoptotic internucleosomal DNA fragmentation is inhibited by actin in complex with gelsolin segment 1; and expression of DNase I in COS cells results in oligonucleosomal fragmentation (Peitsch, et al., 1993; *EMBO J.* 12:371–377).

The findings reported herein demonstrate that cleavage of actin by ICE results in both a markedly decreased ability of actin to inhibit the endonucleolytic activity of DNase I and a diminished ability of actin to polymerize. For example, if in healthy, non-apoptosing cells one of the functions of actin is to inhibit DNase I, then it is conceivable that, at the onset of apoptosis, ICE may reverse this inhibition by cleaving actin into fragments that have a reduced capacity to inhibit the endonucleolytic activity of DNase I. Furthermore, if ICE-cleaved actin is also reduced in its ability to polymerize, then its participation in the formation of the cytoskeleton may also be impaired, leading to the bleb formation, process retraction, and cellular rounding that are characteristic of apoptosis.

The present invention, thus, provides compositions and methods for the coordination of the proteolytic, endonucleolytic, and morphogenetic aspects of apoptosis. Also provided are methods for identifying additional apoptotic substrates, i.e., key cellular proteins that are cleaved by ICE.

More specifically, the present invention provides a method for identifying substrates of the mammalian interleukin-1β converting enzyme (ICE), said method comprising contacting a test compound with an effective amount of ICE under conditions which permit an enzyme-substrate reaction to proceed; and thereafter identifying as substrates those test compounds which are cleaved by ICE. In one embodiment of such method a cellular extract is treated with an effective amount of active ICE. The reaction products generated are subsequently analyzed electrophoretically and compared to control extract. Methods for electrophoretic analysis are well known to those of skill in the art. In a preferred embodiment, 2-dimensional electrophoresis is employed. Such method enables one of skill in the art to identify key cellular proteins that are ICE substrates by electrophoretic shifting of cellular proteins that are cleaved by ICE. The proteins so identified can be isolated using various methods well known to a person of skill in the art. The methods available for the isolation and purification of ICE substrate proteins include, precipitation, gel filtration, ion-exchange, reverse-phase and affinity chromatography. Other well-known methods are described in Deutscher et al., *Guide to Protein Purification: Methods in Enzymology* Vol. 182, (Academic Press, 1990), which is incorporated herein by reference.

In accordance with still another embodiment of the present invention, there is provided a method for identifying compounds which modulate the apoptotic activity of ICE. Such an assay can accommodate the rapid screening of a large number of compounds to determine which compounds, if any, are capable of binding to the ICE recognition site on the actin protein or binding to the active site on ICE. Subsequently, more detailed assays can be carried out with those compounds found to bind, to further determine whether such compounds act as modulators, of ICE activity.

As used herein an "ICE recognition site" is an aspartyl residue on the surface of a protein that is specifically recognized and cleaved by the active site of ICE. In a preferred embodiment, the aspartyl residue is located in the P1 position relative to the cleavage site. For the purposes of the instant invention the "active site of ICE" refers to amino acid residues QACRG (SEQ ID NO:1 ), wherein the active cysteine is located at position 285.

In another embodiment of the invention, there is provided a bioassay for identifying compounds which modulate the apoptotic activity ICE. According to this method, a mixture of actin polypeptides, an amount of DNase I sufficient to form a complex with the actin polypeptide, and an "unknown" or test substance is contacted with an amount of ICE sufficient to cleave the actin polypeptide, the presence and/or absence of free DNase I in the mixture is monitored subsequent to the contact with ICE, the presence of free DNase indicating cleavage of actin and disruption of the actin—DNase I complex and those substances which effect such presence are identified as compounds that modulate the apoptotic activity of ICE.

The present invention further provides a method for producing an actin protein that lacks an ICE recognition site comprising expressing a polynucleotide encoding an amino acid sequence substantially the same as the amino acid sequence of a naturally occurring actin protein, but wherein the encoded protein has at least one amino acid substitution or deletion such that said protein is no longer amenable to cleavage by ICE. Preferred amino acid substitutions and or deletions include, for example, aspartyl residues. Preferred aspartyl residues include, for example, $Asp^{11}$ or $Asp^{244}$.

An example of the means for preparing the invention protein(s) is to express nucleic acids encoding the modified protein in a suitable host cell, such as a bacterial cell, a yeast cell, an amphibian cell (i.e., oocyte), or a mammalian cell, using methods well known in the art, and recovering the expressed polypeptide, again using well-known methods. Invention polypeptides can be isolated directly from cells that have been transformed with nucleic acid encoding the modified actin protein. The invention polypeptide and functional equivalents thereof can also be produced by chemical synthesis. Synthetic polypeptides can be produced using Applied Biosystems, Inc. Model 430A or 431A automatic peptide synthesizer (Foster City, Calif.) employing the chemistry provided by the manufacturer.

The present invention provides an isolated modified actin polypeptide that is not susceptible to ICE-induced cleavage. As used herein, the term "isolated" means a protein molecule free of cellular components and/or contaminants normally associated with a native in vivo environment. Invention proteins can be isolated using various methods well known to a person of skill in the art.

Additionally, the present invention provides isolated nucleic acids encoding an actin protein mutated such that it is lacking one or more ICE recognition sites, and is not susceptible to cleavage by ICE. In a preferred embodiment the mutation is of at least three contiguous nucleic acids encoding an aspartyl residue. The term "nucleic acids" (also referred to as polynucleotides) encompasses RNA as well as single and double-stranded DNA and cDNA. As used herein, the phrase "isolated" means a polynucleotide that is in a form that does not occur in nature.

Further provided are compositions containing a pharmaceutically acceptable carrier and a compound(s) which modulates the apoptotic activity of ICE and a pharmaceutically acceptable carrier. More specifically, such invention compositions can be effectively used to selectively block ICE-induced actin cleavage.

Still further provided are compositions containing a pharmaceutically acceptable carrier and an isolated actin protein lacking an ICE recognition site. These proteins can be recombinantly derived or chemically synthesized.

As used herein, the term "pharmaceutically acceptable carrier" encompasses any of the standard pharmaceutical carriers, such as phosphate buffered saline solution, water and emulsions such as an oil/water or water/oil emulsion, and various types of wetting agents. Methods of administration are well known to those of skill in the art and include, but are not limited to oral administration, parenteral administration and enteral administration. Administration will be in a dosage such that the desired effect is produced.

The present invention also provides methods of alleviating a pathological condition associated with apoptotic mechanisms comprising administering to a subject an amount of an invention composition to prevent ICE-associated apoptosis.

Examples of pathological conditions associated with apoptotic mechanisms include, for example, excessive cell death associated with pathologies such as AIDS, neurodegenerative diseases, and ischemic injury. The abnormal cell death associated with such pathologies can be reduced by invention compositions designed to block apoptosis.

Death of non-renewable post-mitotic cells can be particularly devastating, leading to the considerable mortality and morbidity seen in ischemic conditions such as stroke and myocardial infarction wherein excess tissue damage has been shown to result from the initiation of apoptosis following the restoration of blood flow. Similarly, in neurodegenerative conditions, such as, for example, Alzheimer's disease and traumatic brain injury, neurons frequently succumb to premature apoptosis. Invention methods and compositions are intended to prevent completion of the apoptosis process.

The following examples are intended to illustrate, but not limit, the present invention.

EXAMPLE I
Preparation and ICE Treatment of Cell Extracts

All cells were grown in Dulbecco's modified Eagle's medium (DMEM) with fetal bovine serum (FBS, 10%) and horse serum (HS, 5%) on plastic dishes. At semi-confluency they were washed with and switched to serum-free medium (DMEM) in order to induce apoptosis.

Cells were washed with ice-cold PBS twice and were extracted with Triton X-100® detergent (1%) in Hepes buffer (10 mM, pH=7.5). Supernatants were treated with ICE as follows: 50 µg of cellular protein extracted from semi-confluent cells grown in serum-containing media was incubated with 50 ng of highly purified human recombinant ICE (p20/p10) (Merck, Wayne, N.J.) at 37° C. for 2 hours in the presence of 10 mM dithiothreitol (DTT).

EXAMPLE II
Identification of ICE Substrates

In order to determine whether any of the cellular proteins of relatively high abundance serve as ICE substrates, extracts prepared from PC12 pheochromocytoma cells (29), CSM14.1 cells (conditionally immortalized mesencephalic neuronal cells) (30, 31), and Rat-1 cells (25) were treated with highly purified human recombinant ICE under various conditions. The cleavage products were then analyzed by SDS-polyacrylamide gel electrophoresis.

In comparison to the PC12 cell extracts incubated in buffer without ICE, the extracts incubated with ICE displayed a significant reduction in a major 42 kd protein, with the simultaneous appearance of a protein of approximately 41 kd with the large majority of other bands remaining unchanged in the presence of ICE. Control was incubated in the absence of ICE. A 42 kd protein was identified as actin and the 41 kd protein was identified as an actin cleavage product, by immunoblotting. There was a reduction in 42 kd actin in association with ICE proteolysis, and the appearance of an approximately 41 kd species. A weakly stained actin fragment of approximately 30 kd was also observed on the immunoblots of ICE-treated samples, but not by Coomassie blue staining blue staining, probably due to the presence of other proteins in that region of the gel.

The cleavage of actin in cell extracts by ICE treatment was confirmed by two-dimensional gel electrophoresis. Furthermore, the generation of actin fragments was completely inhibited by protease inhibitors that have been shown to inhibit ICE, including the tetrapeptide aldehyde Ac-Tyr-Val-Ala-Asp-CHO (SEQ. ID NO:2) and the sulfhydryl reagent iodoacetate (Thornberry, et al., 1992; *Nature* 356:768–774), but not by those shown not to inhibit ICE, including leupeptin, antipain, pepstain, E-64, phenylmethylsulfonyl fluoride (Black, et al., 1989; *FEBS* Lett. 247:386–390), and the granzyme B inhibitors human α2-macroglobulin and human α1 protease inhibitor (Poe, et al., 1991; *J. Biol. Chem.* 266:98–103). In addition to PC12 cells, ICE-associated actin fragmentation was also demonstrated in extracts from CSM14.1 cells and Rat-1 cells.

EXAMPLE III
Cleavage of Purified Actin by ICE

In order to determine whether the alterations in the migration of actin were the direct result of cleavage by ICE, α-actin purified from rabbit skeletal muscle (Dr. E. Reisler, University of California, Los Angeles) was incubated in the globular (G-actin) form with purified ICE (ratio of actin:ICE=500:1 wt:wt) from 0 to 90 minutes and the products evaluated by SDS-polyacrylamide gel electrophoresis. The appearance of a 41 kd fragment within 5 minutes, followed by a decrease in the 41 kd fragment in association with the appearance of bands at approximately 30 kd and 14 kd) were noted.

In the presence of ICE, actin was cleaved, resulting in a disappearance of the 42 kd band, and the appearance of bands at approximately 41 kd, 30 kd, and 14 kd. Kinetic studies demonstrated that the 41 kd species appeared first, and then, temporally associated with its decline, the 30 kd and 14 kd bands appeared. Cleavage was inhibited only by protease inhibitors known to inhibit ICE.

It has been determined that ICE cleaves actin in buffer conditions favoring polymerization but the possibility that the cleavage resulted from a small amount of G-actin in equilibrium with its polymerized form cannot be excluded. Therefore it is not known yet whether filamentous actin represents a substrate for ICE.

EXAMPLE IV
Determination of the Major Sites of ICE Cleavage of Actin

In order to determine the major sites of ICE cleavage of actin, ICE-generated actin fragments were isolated from a polyvinylidene membrane, and partial amino acid sequences obtained by Edman degradation and high performance liquid chromatography. The fragment that migrated at approximately 41 kd displayed an amino-terminal sequence of NGSGLV, indicating that it resulted from actin cleavage between $Asp^{11}$-$Asn^{12}$, within the first β-sheet of G-actin (39). The fragment that migrated in the range of 30 kd also displayed the amino-terminal sequence NGSGLV (SEQ ID NO:3), indicating that it resulted from cleavage both at $Asp^{11}$-$Asn^{12}$ and a second site (given the results from the 14 kd fragment, the most likely site would be at $Asp^{244}$-$Gly^{245}$; see below). This interpretation is also compatible with the kinetic studies showing an increase in the 30 kd and 14 kd bands in temporal association with a decrease in the density of the 41 kd band. The fragment that migrated at approximately the 14 kd region had the amino-terminal sequence GQVITI (SEQ ID NO:4), indicating that it resulted from actin cleavage at $Asp^{244}$-$Gly^{245}$, within the loop that stretches from $Glu^{241}$ to $Val^{247}$ (Kabsch, et al., 1990; *Nature* 347:37–44). The sequencing of the 30 kd fragment revealed the presence of another minor protein component (about 10% of the total protein recovered from that apparent molecular weight region of the polyvinylidene membrane) with an amino-terminal sequence of APLNP (SEQ ID NO:5), indicating an additional minor cleavage site at $Glu^{107}$-$Ala^{108}$. Corresponding two-dimensional gels of ICE-cleaved actin confirmed the presence of two different actin fragments of the same apparent molecular weight of 30 kd, but with distinct isoelectric points, in relative abundance of about 10:1 by Coomassie blue staining.

Immunoblots obtained using two different anti-actin antibodies were prepared. Lanes 1 and 2 were incubated with a monoclonal antibody that binds to actin residues 23–34. Lanes 3 and 4 were incubated with a polyclonal antibody that recognizes the carboxy-terminal 11 amino acids of actin. In lanes 1, 3 no ICE was added. In lanes 2, 4 incubation was with purified ICE.

The monoclonal antibody against residues 23–34 (Boehringer Mannheim, Indianapolis, Ind.) bound to the 41 kd and 30 kd fragments (lane 2), in addition to intact actin (lanes 1 and 2), but did not bind to the 14 kd fragment. In contrast, a polyclonal antibody raised against the carboxy-terminal 11 residues of actin (Sigma, St. Louis, Mo.) recognized the 41 kd and 14 kd fragments (lane 4) in addition to intact actin (lanes 3 and 4). A weakly-stained actin fragment of approximately 30 kd was also detectable with the polyclonal antibody (lane 4). Immunoblotting following two-dimensional gel electrophoresis revealed that the major fragment in the 30 kd region was recognized by the monoclonal antibody but not the polyclonal antibody, whereas the converse was true for the minor one. Together with the partial amino acid sequences of cleaved actin fragments described above, these results support the conclusion that two different actin fragments, $Asn^{12}$-$Asp^{244}$ (major) and $Ala^{108}$-$Phe^{375}$ (minor), run at approximately the 30 kd region.

EXAMPLE V
Deoxyribonuclease I Assay

Intact actin or actin cleaved by ICE was incubated with $2 \times 10^{-4}$ units of DNase I (Sigma, St. Louis, Mo.) in Tris buffer (20 mM, pH=7.5) with 1 mM $CaCl_2$ and 1 mM $MgCl_2$ for 5 minutes at 20° C. 0.5 μg pBluescript plasmid DNA (Stratagene, La Jolla, Calif.) was added and incubation continued for 30 minutes at 37° C. DNase I activity was stopped by adding 10 mM EDTA and the products were analyzed by electrophoresis on 1% agarose gels.

ICE-cleaved actin indeed has a diminished capacity to inhibit DNase I. Intact actin or actin cleaved for 90 minutes by ICE were incubated with DNase I. Plasmid DNA was added and incubation continued for 30 minutes and products were analyzed by electrophoresis on 1% agarose gels. Plasmid DNA used as a substrate was digested to oligonucleotides by purified DNase I within 30 minutes. As expected, preincubation of DNase I with intact actin (1.5 μg) for 5 minutes markedly reduced its ability to digest the plasmid. However, actin cleaved with ICE for 90 minutes demonstrated a reduced ability to inhibit DNase I. The level of inhibition exhibited by cleaved actin was approximately equal to that of intact actin diluted 5-fold, indicating approximately 80% reduction in the DNase I inhibition by actin following ICE cleavage. Control incubations without actin demonstrated that ICE neither cleaved DNase I nor affected its endonuclease activity.

EXAMPLE VI
Actin Polymerization Assay

The polymerization of G-actin to filamentous actin (F-actin) can be induced in vitro by magnesium. 10 μM intact actin (control) and 10 μM ICE-cleaved actin were polymerized by the addition of 2 mM $MgCl_2$ and monitored by measuring the associated increase in light scattering of the solution at 660 nm at 23° C. essentially as described in Schwyter, et al., 1989; *Biochemistry* 28:5889–5895.

FIG. 1 illustrates that intact actin rapidly polymerized upon the addition of 2 mM $MgCl_2$ (arrow); however, cleavage of actin by ICE markedly diminished both the rate and the extent of its polymerization. Actin was cleaved by ICE for 90 minutes as in FIG. 2. 10 μM intact actin (control) and 10 μM cleaved actin were polymerized by the addition of 2 mM $MgCl_2$ (arrow) and monitored by light-scattering of the solution at 660 nm at 23° C. Light-scattering intensity data are given in arbitrary units.

EXAMPLE VII
In Vivo Generation of Actin Fragments During Apoptosis

In addition to the demonstration that actin is a substrate for ICE in vitro, preliminary data indicate that apoptosis is associated with cleavage of actin. PC12 cells were washed in and switched to serum-free medium (DMEM). At 0, 24, and 48 hours after the switch, they were extracted by sonication with 1% Triton X-100® detergent in Hepes buffer (10 mM, pH=7.5) containing protease inhibitors in the following final concentrations: bacitracin (0.1 mg/ml); leupeptin (4 μg/ml); pepstatin A (5 μg/ml); antipain (4 μg/ml); soybean trypsin inhibitor (5 μg/ml); iodoacetamide (2 mM); benzethonium chloride (0.1 mM); benzamidine (1 mM); phenylethylsulfonyl fluoride (1 mM).

Immunoblotting data obtained after the induction of apoptosis in PC12 cells by the withdrawal of serum showed that the monoclonal antibody against actin residues 23–34 bound only to intact actin at 0, 24, and 48 hours after serum withdrawal. However, the polyclonal antibody against the carboxy-terminal 11 residues of actin recognized, in addition to intact actin, a fragment of approximately 30 kd, whose abundance relative to the intact actin increased during apoptosis.

Although the invention has been described with reference to the disclosed embodiments, those skilled in the art will readily appreciate that the specific examples taught hereinabove are only illustrative of the invention and that various modifications can be made without departing from the spirit of the invention.

What is claimed is:

1. A method to identify compounds that modulate the apoptotic activity of ICE (interleukin-1β converting enzyme), said method comprising conducting a competitive binding assay employing ICE and a globular actin protein having at least one ICE cleavage site located in the P1 position relative to the cleavage site;
   wherein the ICE has an active site comprising an amino acid sequence as set forth in SEQ ID NO:1 and wherein a compound that reduces binding of the actin and the ICE is identified as modulating the apoptotic activity of ICE.

2. A bioassay for identifying compounds that modulate the apoptotic activity of ICE, said bioassay comprising:
   (a) contacting a mixture comprising
      i) a complex of DNase I and a globular actin polypeptide having at least one ICE cleavage site with an aspartyl residue located in the P1 position relative to the cleavage site, and
      ii) a test compound
      with an amount of ICE having an active site that comprises an amino acid sequence as set forth in SEQ ID NO:1, effective to cleave said actin polypeptide; and
   (b) identifying compounds that cause an increase of free DNase I in said mixture, wherein the increase of free DNase I indicates cleavage of the actin by the compound and diminished capacity of the ICE to inhibit DNase-induced apoptosis.

3. The method according to claim 2 wherein the actin is α-actin.

4. The method of claim 3, wherein the α-actin is obtained from skeletal muscle.

* * * * *